United States Patent
Hauser

[11] Patent Number: 6,155,251
[45] Date of Patent: *Dec. 5, 2000

[54] BREATH COORDINATED INHALER

[75] Inventor: Stephen G. Hauser, Tarzana, Calif.

[73] Assignee: KOS Pharmaceuticals, Inc., Miami, Fla.

[*] Notice: This patent is subject to a terminal disclaimer.

[21] Appl. No.: 09/262,664

[22] Filed: Mar. 4, 1999

Related U.S. Application Data

[63] Continuation of application No. 08/829,466, Mar. 28, 1997, Pat. No. 5,904,139.

[51] Int. Cl.$^7$ .................................................. A61M 11/00
[52] U.S. Cl. .......................... 128/200.23; 128/200.14; 128/203.12
[58] Field of Search ................. 128/200.23, 200.12, 128/200.14, 203.12

[56] References Cited

U.S. PATENT DOCUMENTS

| | | |
|---|---|---|
| 3,302,834 | 2/1967 | Alsop . |
| 3,900,138 | 8/1975 | Phillips . |
| 4,796,614 | 1/1989 | Nowacki et al. . |
| 5,060,643 | 10/1991 | Rich et al. . |
| 5,421,482 | 6/1995 | Garby et al. . |
| 5,447,150 | 9/1995 | Bacon . |
| 5,460,171 | 10/1995 | Presenti et al. . |
| 5,669,376 | 9/1997 | Sioutas . |

FOREIGN PATENT DOCUMENTS 001463014  12/1923  France .

*Primary Examiner*—Dinh X. Nguyen
*Attorney, Agent, or Firm*—Frommer Lawrence & Haug LLP

[57] ABSTRACT

An improved breath coordinated inhaler is provided for administering medication to a patient in aerosol form for respiratory inhalation therapy. The improved inhaler comprises a compact housing adapted to receive and support a medication cannister including a valve assembly actuatable to deliver a dosage of the medication in aerosol form. The housing includes a plunger mounted at a first end thereof for displacing the cannister against a spray nozzle located at a second end of the housing to actuate the valve assembly and deliver the medication through a mouthpiece to the patient. The plunger is associated with a seal arrangement for venting the housing when the plunger is depressed to allow the patient to draw in air in timed relation to the medication delivery, and to substantially re-seal the housing against ingress of contaminants when the plunger is released.

17 Claims, 4 Drawing Sheets

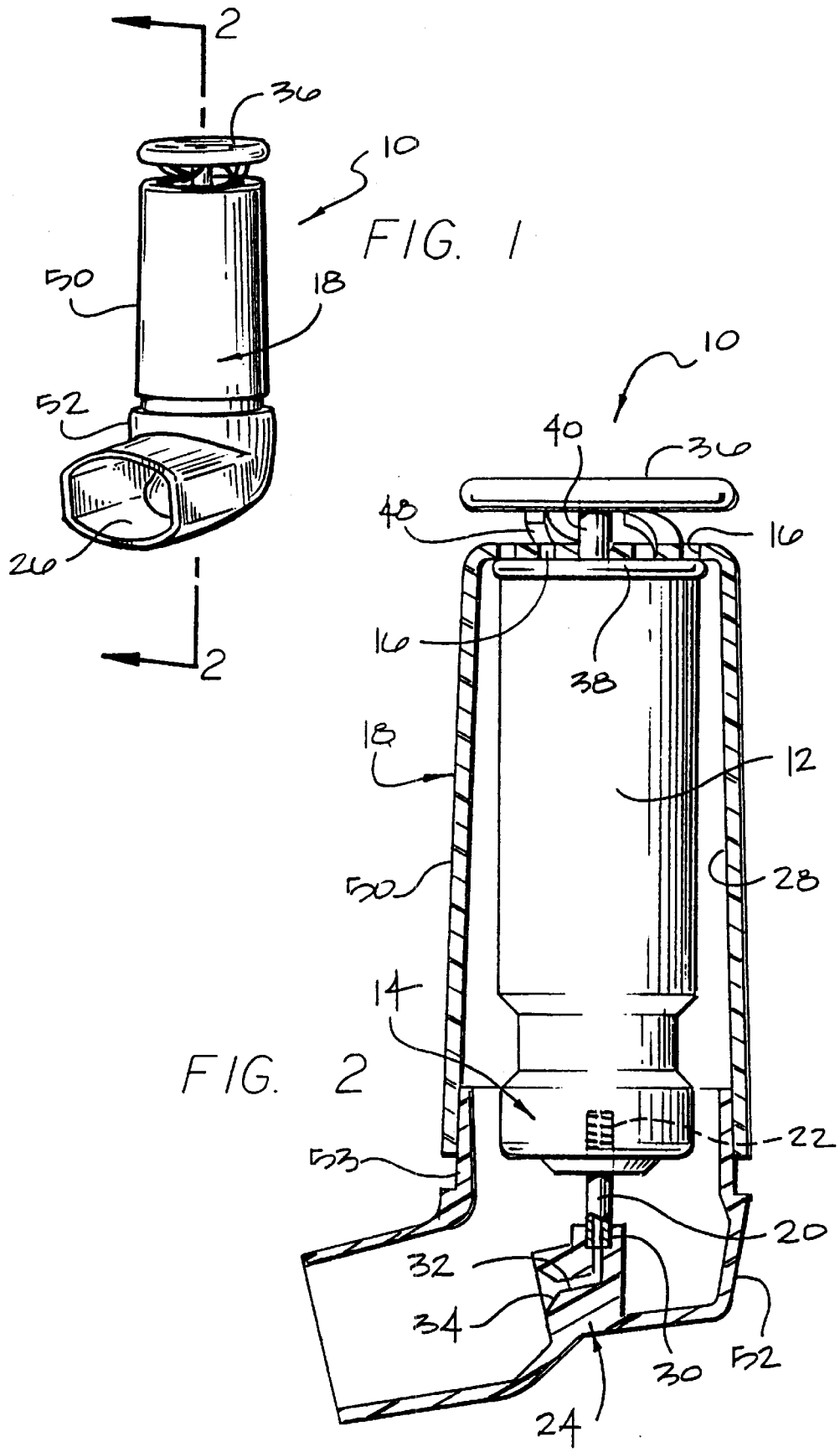

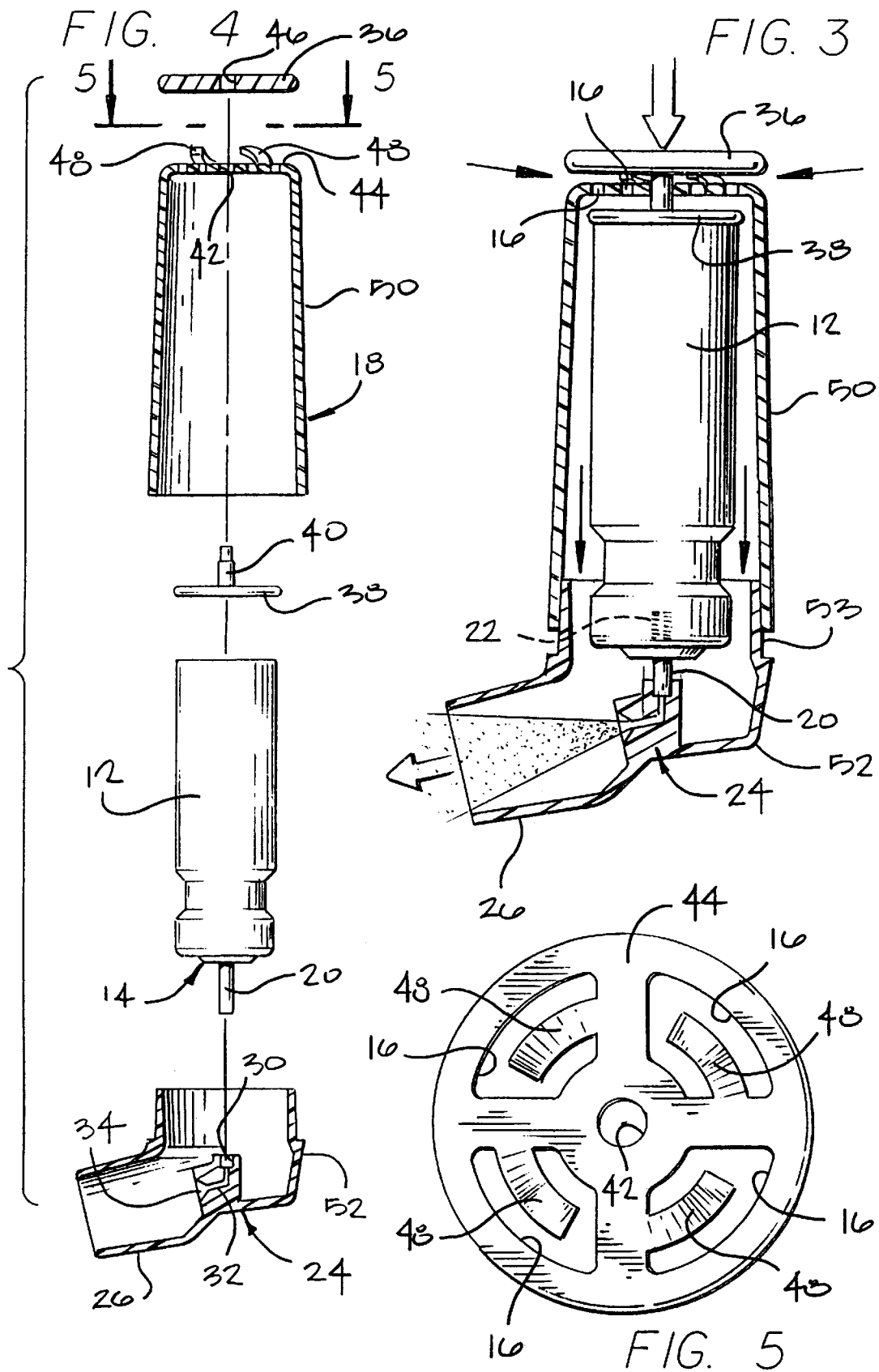

BREATH COORDINATED INHALER

This is a continuation of application Ser. No. 08/829,466, filed on Mar. 28, 1997, now U.S. Pat. No. 5,904,139.

BACKGROUND OF THE INVENTION

This invention relates generally to respiratory inhalers of the type used to deliver a selected medication in aerosol form to a patient, wherein the medication is drawn by inhalation directly into the lungs of the patient. More specifically, this invention relates to an improved inhaler of relatively compact and simplified construction, wherein the inhaler is vented for breath coordinated inhalation of air and medication in a regulated timed manner, but further wherein entry of contaminants into the inhaler between uses is substantially prevented.

Respiratory inhaler devices are generally known in the art for administering a selected medication typically in aerosol form directly into the lungs of a patient to treat a wide variety of medical conditions, such as asthma, bronchitis, and the like, and also for treating other nonrespiratory conditions wherein the lungs represent the site-of-delivery for a selected medication. In one common form, the inhaler comprises a compact hand-held housing for receiving and supporting a cannister containing the selected medication in liquid form under pressure. The cannister is equipped with a reciprocal valve assembly adapted for depression to deliver a single metered dose of the medication through a spray nozzle which propels the medication in aerosol form through a mouthpiece for direct inhalation by the patient. In use, the patient places the mouthpiece in his or her mouth and attempts to inhale in timed relation to manipulation of the cannister and housing to depress the valve assembly, in an effort to draw a substantial portion of the medication deeply into the lungs.

To enhance the delivery of the medication to the patient's lungs, breath coordinated inhalers have been developed wherein air is drawn by the patient through the inhaler housing in synchronized relation to the delivery of the medication. That is, by allowing air to flow through the housing and to be inhaled as the medication is sprayed, the medication can be entrained within a substantial volume of air for better ingestion into the lungs and resultant better administration of the medication. However, the provision of an air pathway through the inhaler housing also provides an open housing construction that is highly susceptible to entry of dirt and other contaminants between uses to administer the medication. In this regard, between uses, the inhaler is often carried about by the patient in a pocket or purse whereat undesired entry of contaminants into the inhaler housing is likely to occur.

Attempts to reconfigure the inhaler housing to accommodate breath coordinated inhalation yet reduce or eliminate undesired entry of contaminants between uses has met with limited success. Vented inhaler housings designed to restrict ingress of contaminants between uses have been relatively complex and thus relatively costly in construction, and further have typically resulted in a substantial increase in the overall size and shape of the inhaler housing. Moreover, absent a substantial increase in the size and shape of the inhaler housing, such vented housings have not provided a simple and reliable way to provide a uniform stroke length for the cannister valve assembly to correspondingly provide uniform doses of the medication, notwithstanding cannister dimension and tolerance variations which occur during normal manufacture.

There exists, therefore, a continuing need for further improvements in breath coordinated inhalers, particularly with respect to providing a relatively simple and compact and cost effective inhaler housing construction that is substantially closed to entry of contaminants between uses, and further wherein the compact inhaler housing is designed to accommodate dimensional variations in the medication-containing cannister. The present invention fulfills these needs and provides further related advantages.

SUMMARY OF THE INVENTION

In accordance with the invention, an improved breath coordinated inhaler is provided for administering medication in aerosol form to a patient. The inhaler comprises a compact housing for receiving and supporting a medication containing cannister or cartridge of a type having a spring-loaded valve assembly actuated by depression to deliver a metered dose of a selected liquid medication contained under pressure within the cannister. The inhaler housing includes a plunger at one end thereof for depression to engage the cartridge in a manner depressing the valve assembly against a spray nozzle to release the medication dose through a mouthpiece at an opposite end of the housing. The plunger is associated with a seal arrangement which opens to provide an air pathway through the housing for breath coordinated inhalation when the plunger is depressed, and which closes upon release of the plunger to substantially prevent entry of dirt and other contaminants into the inhaler housing between uses. With this construction, the air pathway is closed when the plunger is not depressed, such that the patient can inhale the air-entrained medication only when the plunger is depressed to open the air pathway.

In the preferred form of the invention, the inhaler housing has a hollow interior adapted to receive the medication cannister in an inverted orientation with a tubular stem of the valve assembly engaging the spray nozzle formed within the housing at a lower end thereof generally adjacent to the mouthpiece. The upper end of the inverted cannister engages a seal disk mounted within the housing for movement between an open position permitting air flow through one or more vents disposed in the upper end of the housing, and a closed position substantially preventing air flow through said vent. The seal disk is displaced by depression of the plunger for movement from the closed position to the open position, and to displace the cannister relative to the spray nozzle to depress the cannister valve assembly. Accordingly, plunger depression opens the housing vent and operates the cannister valve assembly in synchronized relation to permit the patient to inhale via the mouthpiece a substantial air volume with the medication entrained therein. When the plunger is released, a spring may be provided for return of the seal disk to its original position closing the vent. Alternately, the spring-loaded valve assembly of the cannister may be used for urging the cannister against the seal disk for return to the normal position closing the vent.

The inhaler housing is formed from a pair of slidably intermitting housing members assembled together with the medication cannister therein. These housing members may be slidably press-fitted or alternately adhesively connected. In either case, the interfitting housing members accommodate dimensional tolerance variations in the medication cannister, thereby insuring plunger depression sufficient to displace the cannister valve assembly through a full stroke each time medication is delivered to the patient.

Other features and advantages of the invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is a perspective view of a breath coordinated inhaler embodying the novel features of the invention;

FIG. 2 is a vertical sectional view taken generally on the line 2—2 of FIG. 1;

FIG. 3 is a vertical sectional view similar to FIG. 2, and illustrating depression of a plunger to deliver a dosage of medication to a patient;

FIG. 4 is an exploded vertical sectional view showing assembly of the inhaler components;

FIG. 5 is an enlarged top plan view of a housing for the inhaler, taken generally on the line 5—5 of FIG. 4;

DETAILED DESCRIPTION OF THE PREFERRED EMBODIMENTS

Figure 6:
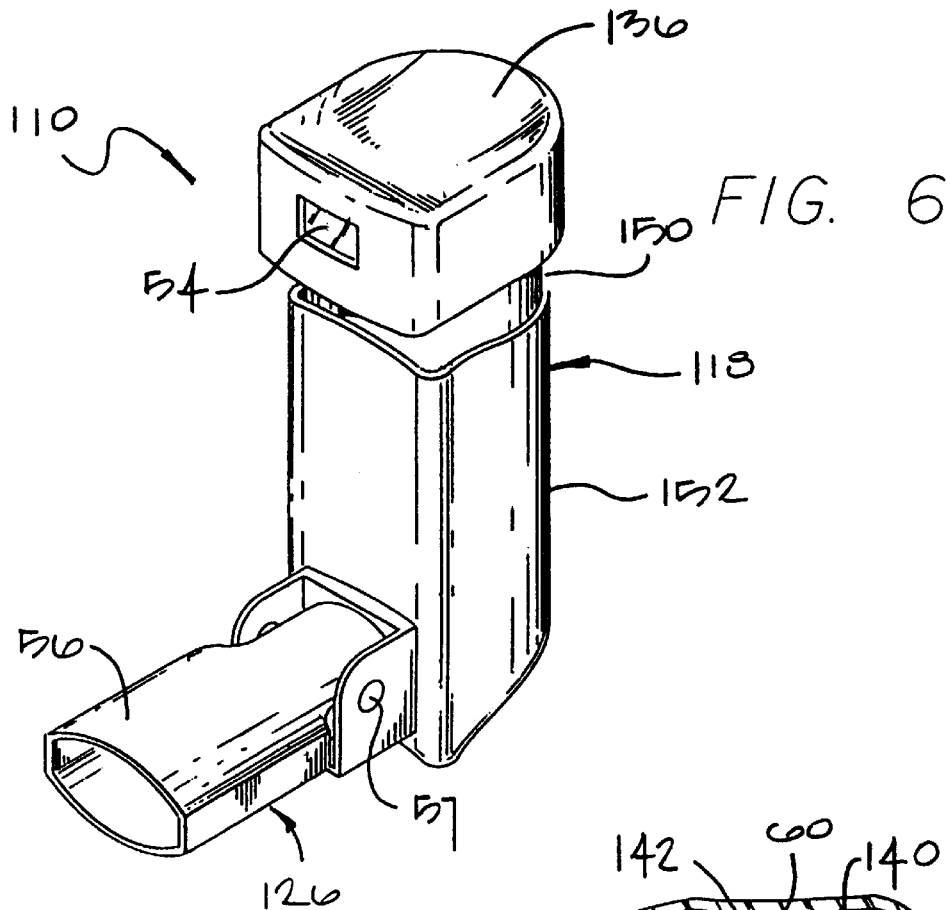
FIG. 6 is a perspective view showing one alternative preferred form of the invention.

As shown in the exemplary drawings, an improved inhaler referred to generally by the reference numeral 10 in FIG. 1 is provided for breath coordinated inhalation of a selected medication used for respiratory therapy. The improved inhaler 10 is adapted to receive and support a compact cannister or cartridge 12 (FIGS. 2–4) containing the selected medication in liquid form under pressure and including a spring-loaded valve assembly 14 for delivering the medication in metered doses. The inhaler 10 includes one or more vents 16 located in the end of an inhaler housing 18, wherein these vents 16 are normally closed to prevent undesired entry of dirt and other contaminants into the interior of the inhaler housing. However, when the inhaler is operated as will be described to deliver a dose of the medication, the vents are opened in synchronized relation to operation of the cannister valve assembly 14, to permit a patient to inhale a significant volume of air with the medication dose entrained therein.

The medication cannister 12 comprises a conventional and widely used product in the form of a small and typically metal cannister containing the selected medication in liquid form under pressure, for delivery of the medication to the patient in the form of an aerosol spray. The cannister 12 normally includes the valve assembly 14 mounted directly into an open end of the cannister, as by roll forming the cannister to capture and retain the valve assembly components. As depicted in FIGS. 2–4, the valve assembly includes a reciprocal tubular stem 20 associated with internally mounted valve elements (not shown) including a spring 22 for spray delivery of a metered dose of the medication each time the stem is depressed. This medication cannister construction and operation is well known in the art, and thus is not further shown or described herein.

In general terms, the inhaler housing 18 is sized and shaped for receiving and supporting the medication cartridge 12 in an inverted orientation, with the tubular stem 20 of the valve assembly 14 seated within a sump forming a spray nozzle 24 located within the housing 18 at a lower end thereof and in a position adjacent to an open mouthpiece 26. More particularly, the inhaler housing 18 is constructed with a relatively compact size and shape, and is conveniently formed from a molded plastic or the like. The housing 18 defines a hollow interior 28 for receiving the cannister 12, with the spray nozzle 24 formed integrally with a lower housing wall. The spray nozzle 24 defines an upwardly open port 30 sized for slide-fit reception of the end of the cannister stem 20 in a position seated upon a small shoulder. The open port 30 is disposed in flow communication with a nozzle orifice 32 and associated expansion spray segment 34 for directing the aerosol dosage of the medication outwardly to a patient through the open mouthpiece 26, as viewed in FIG. 3. The housing is sized to permit air flow therethrough, from the vent 16 to the mouthpiece 26, when the vents 16 are opened as will be described.

The inhaler housing 18 carries a plunger 36 mounted at an upper end thereof in an exposed position outside the housing. The plunger 36 is provided for displacing the medication cannister 12 in a downward direction within the housing, resulting in depression of the tubular stem 20 of the valve assembly 14. The plunger 36 is thus manipulated to operate the valve assembly 14 to deliver a dose of the medication through the mouthpiece. In use, the patient places the mouthpiece 26 into his or her mouth (not shown), and then depresses the plunger 36 to deliver the dose of the medication through the mouthpiece. Substantially at the time of medication delivery, the patient attempts to inhale for the purpose of drawing a substantial portion of the sprayed medication deeply into the lungs.

The plunger 36 is associated with a seal arrangement designed to normally close the inhaler housing 18 against entry of dirt and other contaminants. However, the seal arrangement is operated by the plunger 36 to open the vents 16 when the plunger is depressed to permit air flow into the top of the housing when medication is delivered to the patient. Accordingly, when the plunger is depressed, the upper end of the housing 18 is opened to air flow so that the patient can inhale a substantial volume of air in coordinated or synchronized relation to the medication. The coordinated inhalation of air and medication entrains the medication in the air volume and thus enhances delivery of the medication to deep or lower lung zones.

As shown best in FIGS. 2–5, the seal arrangement comprises a seal disk 38 mounted within the inhaler housing 18 at the inboard side of the housing upper end. The seal disk, which may be formed from or otherwise lined with a resilient seal material, has a size and shape to overlie the vents 16 in order to close and seal the vents when the seal disk 38 engages the housing upper end. A central stem 40 protrudes upwardly from the seal disk 38 for passage through a central port 42 formed in an upper end wall 44 of the housing 18, and subsequent connection as by press-fit or adhesive attachment within an aperture 46 formed in the disk-shaped plunger 36. As shown, the upper end wall 44 of the housing includes a plurality of upwardly arched leaf-type springs 48 which are conveniently formed integrally with the end wall 44, and which bias the plunger 36 upwardly to a normal position carrying the seal disk 38 into sealed engagement with the inboard side of the end wall 44 to close the vents 16. Alternately, it will be recognized that the spring 22 of the cannister valve assembly 14 provides a similar biasing force urging the cannister upwardly to carry the seal disk 38 toward the normal position closing the vents 16, whereby the leaf springs 48 or other spring devices at the top of the housing 18 can be omitted.

In operation, the seal disk 38 is normally retained by the spring force in the closed position sealed against the inboard side of the upper end wall 44 of the inhaler housing 18. In addition, a closure cap (not shown) is also normally provided for closing the mouthpiece 26 at the lower end of the housing 18. Accordingly, the interior 28 of the inhaler housing 18 is normally closed against entry of dirt and the like which can otherwise enter and contaminate the inhaler as the device is carried about by the patient in a pocket or purse. However, when a dose of the medication is desired, removal of the referenced closure cap and mere depression of the plunger 36 opens the vents 16 to allow a substantial volume of air to be drawn into and through the housing interior 28 and further through the mouthpiece 26, in synchronized or timed relation to the plunger-caused displacement of the cannister to deliver the dose of the medication. In this regard, the open area defined by the vents 16 can be closely selected and designed to regulate the air volume drawn through the housing for medication entrainment. Similarly, the geometry of the plunger 36 and the seal disk 38 can be tailored to regulate the timing between the opening of the vents 16 and the actual delivery of the medication dose for substantially optimum entrainment of the medication and administration to deep lung zones. When the plunger 36 is released, the spring force automatically returns the seal disk 38 to the closed position sealing the vents 16.

In accordance with a further aspect of the invention, the inhaler housing 18 can be designed to accommodate variations in the specific height dimension of the medication cannister 12, thereby to accommodate manufacturing tolerance variations which could otherwise affect the displacement stroke length of the cannister when the plunger 36 is depressed. More particularly, as shown in FIGS. 1–3, the preferred housing construction comprises a slidably interfitting generally cup-shaped pair of upper and lower housing members 50 and 52, with matingly overlapping segments referenced by arrow 53, wherein these overlapping segments 53 can be press-fitted together or adhesively interconnected. The overlapping segments 53 are sized to provide a longitudinal tolerance sufficient to accommodate normal height variations in the medication cannister 12, so that the cannister is firmly seated at both the opposite ends thereof with the tubular stem 20 seated within the spray nozzle 24 and an upper end engaging the seal disk 38. In this way, the seal disk 38 is securely retained in sealed relation with the housing end wall 44 in the normal closed position. In addition, a full stroke length of the cannister 12 and the associated stem 20 is assured each time the plunger 36 is depressed, for delivery of the full metered dose of the medication to the patient. In this arrangement, by positioning the plunger 36 at the upper end of the housing 18, a full stroke length is provided without requiring any significant increase to the overall size, shape or profile of the inhaler device.

Figure 7:
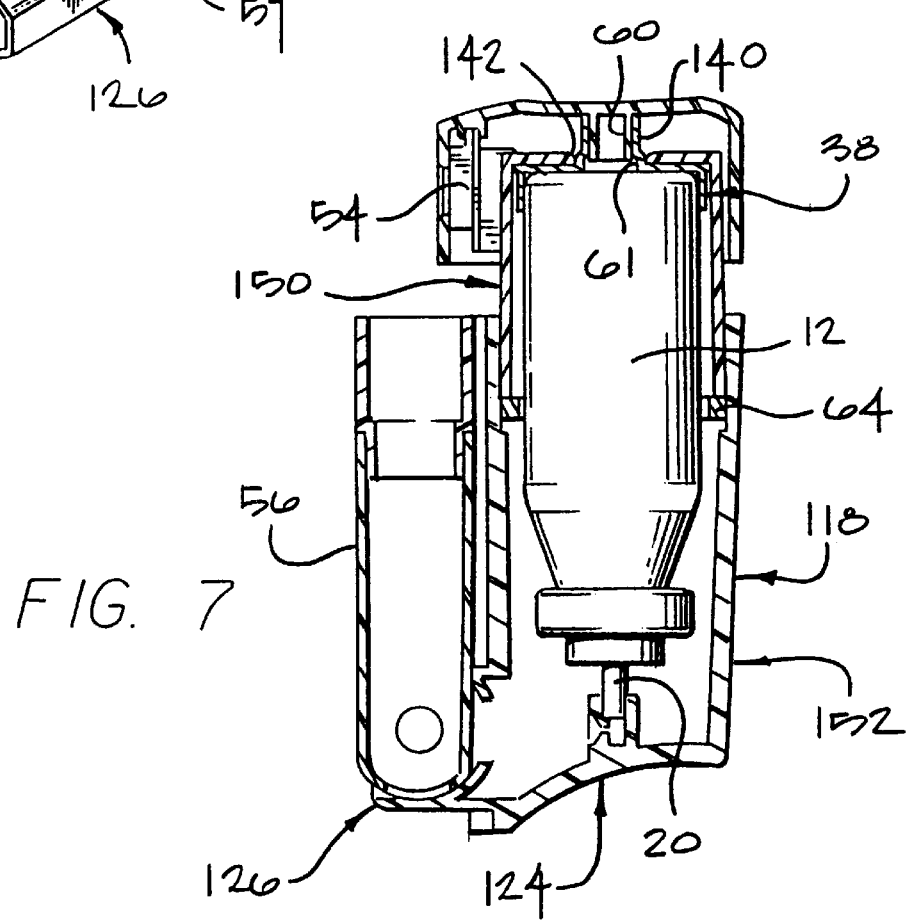
FIG. 7 is a vertical sectional view of the embodiment of FIG. 6.
Figure 8:
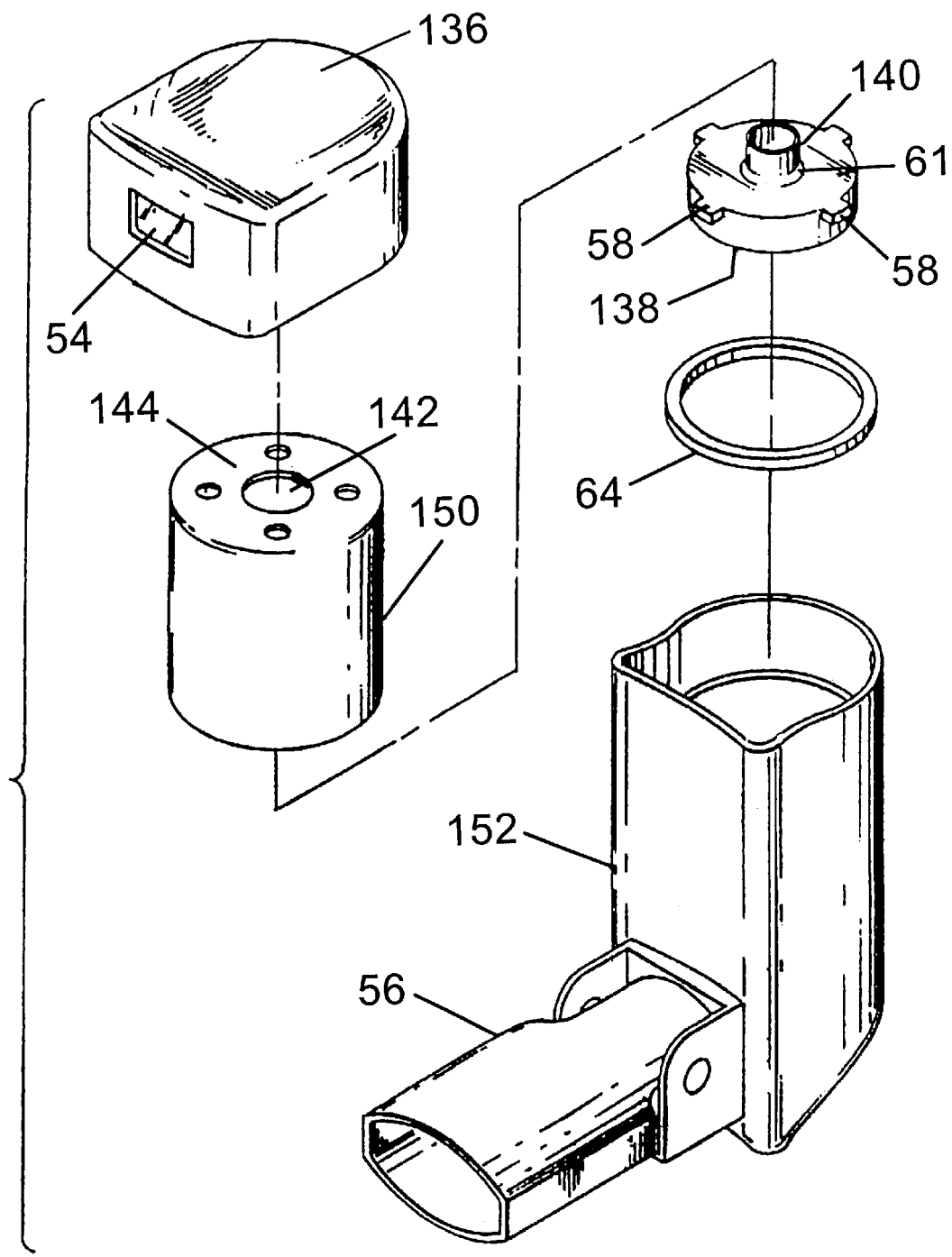
FIG. 8 is an exploded perspective view depicting assembly of the components of the embodiment of FIG. 6.

An alternative preferred form of the invention is shown in FIGS. 6–8, wherein modified components corresponding in structure and function to those shown and described in FIGS. 1–5 are identified by common reference numerals increased by 100. As shown, a modified breath coordinated inhaler 110 is provided with a plunger 136 adapted to include a counter 54 to track the number of medication doses delivered from the device. The inhaler 110 also includes a modified mouthpiece 126 including an elongated inhaler tube 56 mounted onto the inhaler housing 118 by a pivot pin 57 for pivoting movement between a stored position (FIG. 7) and an outwardly projecting active position for use (FIGS. 6 and 8).

The modified inhaler 110 includes the hollow inhaler housing 118 with a spray nozzle 124 formed therein at a lower end thereof adjacent to the open mouthpiece 126. The spray nozzle 124 is adapted to receive the tubular stem 20 of an inverted medication cannister 12 in the same manner as previously shown and described. The inhaler 118 is sized and shaped for close-fit reception of the cannister 12 and includes the plunger 136 and vented seal arrangement at the housing upper end.

More particularly, as shown best in FIGS. 7 and 8, a modified seal disk 138 is mounted within the inhaler housing and comprises a generally cup-shaped element inverted to fit over the upper end of the inverted medication cartridge 12. The seal disk 138 defines an outer rim to include a plurality of short spacer tabs 58 for providing an air pathway between the outer periphery of the seal disk 138 and the inner surface of an upper housing member 150. An upwardly projecting stem 140 is formed on the seal disk 138 and extends through an open port 142 in the upper housing member 150 for press-fit or snap-fit or adhesive attachment to a boss 60 on the plunger 136. A lower portion of this stem 140 is defined by a larger diameter seal ring segment 61 having a size and shape to sealingly close the housing port 142 when the seal disk 138 is positioned substantially in engagement with the inboard side of the upper end wall 144 of the upper housing member 150.

When the plunger 136 is depressed, the seal disk 138 and the medication cannister 12 are displaced through a downward stroke in the same manner as previously described with respect to FIGS. 1–5. In particular, the downward movement of the seal disk 138 moves the seal ring segment 61 out of the housing port 142 to permit air flow into and through the inhaler housing 118. The corresponding downward movement of the cannister 12 results in discharge of a metered dose of the medication to the mouthpiece. The medication is thus entrained within the air flow for inhalation by the patient into the patient's lungs. Importantly, the geometry of the seal ring segment 61 and the related housing port 142 can be closely controlled to regulate the air volume drawn through the device and further to control the timing of medication discharge relative to venting of the housing via the port 142.

The plunger 136 conveniently includes the counter 54 adapted for detecting each downward stroke of the plunger to deliver a medication dose. An electronic display is provided on a side of the plunger to indicate the number of doses which have been delivered, or the number of doses remaining in the cannister. The particular mechanism used in the counter to detect downward plunger strokes may vary and will be understood by persons skilled in the art. Moreover, it will be recognized that the counter device is optional and may be omitted.

The inhaler housing 118 comprises the slidably interfitting upper and lower housing members 150 and 152 for accommodating dimensional variations in the specific medication cannister 12, as previously described. In the embodiment of FIGS. 6–8, the upper housing member 150 is shown for sliding fit into a matingly shaped lower housing member 152. A stop ring 64 is provided within the lower housing member 152 to provide a mechanical stop preventing over-insertion of the upper housing member 150 with the plunger 136 mounted thereon.

More particularly, in the embodiment of FIGS. 6–8, initial assembly of the upper housing members 150 is performed with the plunger 136 and the related seal disk 138. This subassembly is then adapted for installation as a unit with the lower housing member 152. In this regard, in an assembly line production environment, a specific medication cannister 12 can be associated with a lower housing member 152, and the stop ring 64 is inserted into the lower housing member 152 at a specific depth corresponding to the height dimension of the matched cannister 12. The stop ring 64 can be installed as a simple press-fit, or desirably attached by adhesive bonding or sonic welding or the like. Thereafter, the lower housing member 152 and its associated medication cannister 12 can be assembled with an upper housing member subassembly as described above for packaging and shipment. The stop ring 64 provides a fixed mechanical stop for correct sliding fit of the upper and lower housing members 150, 152 according to the actual height dimension of the cannister 12. The housing members can be periodically disassembled for cleaning, if desired, and subsequently re-assembled in the correct slide-fit relation.

The improved breath coordinated inhaler of the present invention thus provides a relatively simple construction for permitting patient inhalation of air with an entrained dose of the selected medication, resulting in a highly efficacious administration of the medication. However, the invention further provides an effective seal arrangement for substantially closing the interior of the inhaler housing between uses, to substantially prevent ingress of dirt and other contaminants. The vent and seal arrangement is provided at the upper end of the inhaler housing to result in a highly compact inhaler construction which is relatively cost efficient to produce and assemble in production quantities, and which further is adapted to accommodate tolerance variations in standard medication cannisters.

A variety of further modifications and improvements in and to the breath coordinated inhaler of the present invention will be apparent to those persons skilled in the art. Accordingly, no limitation on the invention is intended by way of the foregoing description and accompanying drawings, except as set forth in the appended claims.

What is claimed is:

1. A breath coordinated inhaler for use with a medication cannister containing a selected medication under pressure and having a spring-loaded valve assembly for delivering a metered dose of the medication in aerosol form, said inhaler comprising:

a housing having a hollow interior for receiving and supporting the medication cannister in an inverted orientation, said housing defining an upper end with at least one vent formed therein and a lower end, said housing further defining an open mouthpiece generally at said lower end;

spray nozzle means within said housing generally at said lower end for engaging the cannister valve assembly;

a non unitary seal means disposed within said housing generally at said upper end for normally overlaying and closing said vent;

spring means associated with said seal means for normally retaining said seal means in a closed position overlying and closing said vent; and plunger means mounted at said housing upper end and coupled to said seal means, said plunger means being depressable to move said seal means to an open position spaced from said vent and further to move the medication cannister within said housing whereby the cannister valve assembly is operated by said spray nozzle means to deliver a dose of the medication through said mouthpiece.

2. The breath coordinated inhaler of claim 1 wherein said spring means reacts between said housing and said plunger means.

3. The breath coordinated inhaler of claim 2 wherein said spring means is formed integrally with said housing.

4. The breath coordinated inhaler of claim 1 wherein said seal means comprises a seal disk mounted within said housing at an inboard side of said housing upper end.

5. The breath coordinated inhaler of claim 4 wherein said seal disk is connected to said plunger means by a stem extending through an open port formed in said housing upper end.

6. The breath coordinated inhaler of claim 1 wherein said housing is formed by a pair of slidably interfitting, generally cup-shaped housing members.

7. The breath coordinated inhaler of claim 6 further including stop means for limiting sliding interfit of said housing members.

8. The breath coordinated inhaler of claim 7 wherein said stop means comprises a stop ring mounted within one of said housing members.

9. The breath coordinated inhaler of claim 1 wherein said seal means comprises a seal disk mounted within said housing at an inboard side of said upper end, and a connector stem extending through an open port formed in said housing upper end to interconnect said seal disk and said plunger means, said connector stem having a cross sectional size whereby said open port forms said vent when said seal disk is displaced by said plunger means to said open position.

10. The breath coordinated inhaler of claim 9 wherein said seal disk cooperates with said housing to define an air pathway between said vent and said mouthpiece.

11. The breath coordinated inhaler of claim 1 wherein said plunger means is depressable to move said seal means against the medication cannister to displace the cannister within said housing.

12. A breath coordinated inhaler, comprising;

a medication cannister containing a selected medication under pressure and including a spring-loaded valve assembly at one end thereof for depression to deliver a metered dose of the medication;

an inhaler housing having a hollow interior for receiving and supporting said cannister, said housing defining an upper end with at least one vent formed therein and a lower end, said housing further defining an open mouthpiece generally at said lower end;

a spray nozzle mounted within said housing generally at said lower end for engaging said cannister valve assembly;

a non unitary seal member disposed within said housing generally at said upper end and movable between a closed position overlying and closing said vent and an open position spaced from said vent to permit air flow through said vent and further through said housing to said mouthpiece;

a spring means on said housing associated with said seal member for urging said seal member normally to said closed position; and a plunger connected to said seal member and disposed outside said housing at said upper end thereof, said plunger means being depressable to move said seal member from said closed position to an open position and further to move said seal member against said cannister whereby said cannister valve assembly is actuated by said spray nozzle to deliver a metered dose of the medication through said mouthpiece, said valve assembly providing a spring force urging said seal member to return to said closed position upon release of said plunger.

13. The breath coordinated inhaler of claim 12 wherein said seal member is connected to said plunger by a stem extending through an open port formed in said housing upper end.

14. The breath coordinated inhaler of claim 13 wherein said stem has a cross sectional size whereby said open port forms said vent when said seal member is in said open position.

15. The breath coordinated inhaler of claim 12 wherein said housing is formed by a pair of slidably interfitting, generally cup-shaped housing members.

16. The breath coordinated inhaler of claim 15 further including stop means for limiting sliding interfit between said housing members.

17. The breath coordinated inhaler of claim 16 wherein said stop means comprises a stop ring mounted within one of said housing members.

\* \* \* \* \*